United States Patent [19]

Young

[11] 4,301,317
[45] Nov. 17, 1981

[54] PREPARATION OF 2-PHENYLALKANES

[75] Inventor: Lewis B. Young, Skillman, N.J.

[73] Assignee: Mobil Oil Corporation, New York, N.Y.

[21] Appl. No.: 96,095

[22] Filed: Nov. 20, 1979

[51] Int. Cl.³ .................... C07C 2/64; C07C 15/107
[52] U.S. Cl. .................................. 585/455; 585/467
[58] Field of Search ................. 585/455, 467, 323

[56] References Cited

U.S. PATENT DOCUMENTS

| | | | |
|---|---|---|---|
| 3,251,897 | 5/1966 | Wise | 585/455 |
| 3,474,154 | 10/1969 | Yamanaka et al. | 585/323 |
| 3,755,483 | 8/1973 | Burress | 585/467 |
| 3,962,364 | 6/1976 | Young | 585/467 |
| 4,016,218 | 4/1977 | Haag et al. | 585/467 |

FOREIGN PATENT DOCUMENTS

| | | |
|---|---|---|
| 12514 | 6/1980 | European Pat. Off. |
| 1069242 | 5/1967 | United Kingdom |
| 1132859 | 11/1968 | United Kingdom |
| 1403329 | 8/1975 | United Kingdom |

*Primary Examiner*—Curtis R. Davis
*Attorney, Agent, or Firm*—Charles A. Huggett; Ronald J. Cier; George W. Allen

[57] ABSTRACT

A process for the selective alkylation of substituted or unsubstituted benzene compounds with relatively long chain length alkylating agents to produce phenylalkanes having an improved yield of the 2-phenylkane isomer. The reaction is carried out in the presence of crystalline zeolite catalysts characterized by channels or networks of pores having openings with a major dimension of 6–7 angstroms.

11 Claims, No Drawings

PREPARATION OF 2-PHENYLALKANES

BACKGROUND OF THE INVENTION

1. Field of the Invention

This invention is concerned with alkylation of aromatic compounds and, in particular, it is directed to a method for selective production of 2-phenylalkanes.

2. Description of the Prior Art

Conventional Friedel-Crafts alkylations of aromatic compounds with linear olefins, carried out in the presence of $AlCl_3$ or other Lewis acid as catalyst, are known to produce linear secondary phenylalkanes which are typically a mixture of all of the conceivable positional isomers-i.e. 2-phenyl, 3-phenyl, 4-phenyl, etc. Primary phenylalkanes and products with side chain branching are not usually formed. For example, the reaction of benzene and 1-dodecene in the presence of $AlCl_3$ gives a product mix as follows:

| $AlCl_3$ Benzene + $1-C_{12}$ = → #-Phenyldodecane | |
|---|---|
| Position of Phenyl Substituent, # | Composition |
| 1 | 0% |
| 2 | 30% |
| 3 | 19% |
| 4 | 17% |
| 5 | 17% |
| 6 | 17% |

The composition of the phenyldodecane mixture is somewhat dependent upon the acid catalyst involved. For instance, $H_2SO_4$ catalyst has been reported to result in 41% 2-phenyldodecane while HF yields 20% 2-phenyldodecane in the phenyldodecane product mix. Similar results can be shown for other alkylations involving relatively large (i.e. $>C_5$) alkylating agents.

Linear alkylbenzenes are produced commercially via the Friedel-Crafts route in quantities exceeding 500 million pounds per year. The vast majority of this production is subsequently sulfonated to satisfy the demand for alkylbenzene sulfonic acid based detergents for the detergent industry. The 2-phenylalkane sulfonates are known to be the most biodegradable of the respective isomers and hence, if they could be selectively produced at reasonable cost, would be of considerable utility in applications where biodegradability is a consideration.

SUMMARY OF THE INVENTION

It has now been discovered that the reaction of aromatic compounds with relatively long-chain alkylating agents, when carried out in the presence of certain crystalline zeolite materials as catalysts, will result in linear phenylalkanes in which the content of the 2-phenyl substituted linear alkane isomer is in excess of its expected equilibrium concentration. The crystalline zeolites utilizable in this process are characterized by channels or networks of pores therethru, the major dimension of the opening to the channels or networks of pores being between about 6 angstrom units and about 7 angstrom units. Specific preferred catalysts include cancrinite, gmelinite, mordenite, and offretite, and synthetic and naturally occurring isotypes thereof. A particularly preferred zeolite, whose crystallographic structure is unknown at the present time, is the synthetic zeolite ZSM-12.

The process is carried out by contacting the aromatic compound, which may be a substituted or unsubstituted benzene, with the alkylating agent in the presence of the specified type of zeolite catalyst and under suitable alkylation conditions. Preferred conditions include a temperature of between about 50° C. and 500° C. and a pressure of about $2.5 \times 10^4$ $N/m^2$ to $2.5 \times 10^7$ $N/m^2$ (0.25-250 atmospheres). Suitable alkylating agents include alkyl halides, olefins and alcohols which have a linear "backbone" of at least five carbon atoms and preferably from about 6 to about 20 carbon atoms.

DESCRIPTION OF SPECIFIC EMBODIMENTS

It is contemplated that alkylating agents useful in the process of this invention will include any aliphatic or aromatic organic compund, having one or more available alkyl groups of at least five carbon atoms, which are capable of reacting with an aromatic compound. Useful alkylating agents include, for example, alkyl halides, olefins or alcohols having a linear hydrocarbon chain length or "backbone" of at least five (5) carbon atoms, and preferably from about 6 to about 20 carbon atoms. Olefins are the preferred alkylating agents, although one may plainly substitute any other hydrocarbon material which will generate unsaturated carbon atoms in the presence of the disclosed alkylation catalysts.

The aromatic compounds which are to be reacted with the foregoing alkylating agents to yield 2-phenylalkanes by the process disclosed herein are benzene compounds. These benzene compounds may be unsubstituted, or they may carry from 1 to 2 substituents on the ring structure. If substituted, the substituent may be an alkyl group having from 1 to 10 carbon atoms therein, or may be a halide, an alkoxy, an aryl group, and so forth, or any combination of such substituents.

The zeolites utilized herein may be either naturally occurring or synthetic and include, by way of example, cancrinite, gmelinite, mordenite, dealuminized mordenite, offretite and ZSM-12. Also contemplated as being included herein are synthetic and naturally occurring isotypes of such zeolite materials, such as: zeolite S, zeolite Na-S, zeolite Na-D, Ptilolite, Zeolon, zeolite O, TMA-offretite, and others.

The crystal structure of the class of zeolites suitable for use as catalysts in the process of this invention is such as to provide access to and egress from the intracrystalline free space of the zeolites by virtue of having channels or networks of pores (hereinafter referred to as pores), the openings thereto preferably having a major dimension of between about 6A and about 7A. The zeolites utilized herein are further characterized by pore apertures of about a size as would be provided by 12-member rings of silicon or aluminum atoms. It will be understood, of course, that these rings are those formed by the regular disposition of the tetrahedra making up the anionic framework of the crystalline zeolite, the silicon or aluminum atoms forming the centers of the tetrahedra and being themselves bonded together by oxygen atoms.

The pores characterizing the zeolites useful in the present process may be substantially circular, such as is the situation with respect to cancrinite which has uniform pores of about 6.2 angstroms, or may be somewhat elliptical, such as in mordenite which has pores of approximately 6.7 by 7.0 angstroms. It should be understood that, in any case, the zeolites used as catalysts in the process of this invention have a major pore dimension intermediate between that of the large pore zeolites, such as the X and Y zeolites, and the relatively small pore size zeolites ZSM-5 and ZSM-11, and preferably between about 6A and about 7A. With the exception of zeolite ZSM-12, the pore size dimensions and crystal structures of the above zeolites are those specified in ATLAS OF ZEOLITE STRUCTURE TYPES by W. M. Meier and D. H. Olson, published by the Structure Commission of the International Zeolite Association (1978) and distributed by Polycrystal Book Service, Pittsburgh, Pa.

ZSM-12, the structure and pore size of which is unknown at the present time, is described in U.S. Pat. No. 3,832,449. That description, and in particular the characteristic crystal X-ray diffraction pattern disclosed therein, is incorporated herein by reference.

The zeolites useful in the conversion process of this invention generally have at least 10 percent of the cationic sites thereof occupied by ions other than alkali or alkaline-earth metals. Typical but non-limiting replacing ions include ammonium, hydrogen, rare earth, zinc, copper and aluminum. Of this group, particular preference is accorded ammonium, hydrogen, rare earth or combinations thereof. In a preferred embodiment, the zeolites are converted to the predominantly hydrogen form, generally by replacement of the alkali metal or other ion originally present with hydrogen ion precursors, e.g. ammonium ions, which upon calcination yield the hydrogen form. This exchange is conveniently carried out by contact of the zeolite with an ammonium salt solution, e.g. ammonium chloride, utilizing well known ion exchange techniques. The extent of replacement is such as to produce a zeolite material in which at least 50 percent of the cationic sites are occupied by hydrogen ions.

The zeolites may be subjected to various chemical treatments, including alumina extraction and combination with one or more metal components, particularly the metals of Groups IIB, III, IV, VI, VII and VIII. It is also contemplated that the zeolites may, in some instances, desirably be subjected to thermal treatment, including steaming or calcination in air, hydrogen or an inert gas, e.g. nitrogen or helium.

An especially useful modifying treatment entails steaming of the zeolite by contact with an atmosphere containing from about 5 to about 100 percent steam at a temperature of from about 250° to 1000° C. Steaming may last for a period of between about 0.25 and about 100 hours and may be conducted at pressures ranging from sub-atmospheric to several hundred atmospheres to reduce the alpha value of the zeolite to less than 500, and preferably less than 20, but greater than zero.

In practicing the desired conversion process, it may be useful to incorporate the above-described intermediate pore size crystalline zeolites in another material resistant to the temperature and other conditions employed in the process. Such matrix materials include synthetic or naturally occurring substances as well as inorganic materials such as clay, silica, and/or metal oxides. The latter may be either naturally occurring or in the form of gels or gelatinous precipitates including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment, or chemical modification.

In addition to the foregoing materials, the intermediate pore size zeolites employed herein may be compounded with a porous matrix material, such as alumina, silica-alumina, silica-magnesia, silica-zirconia, silica-thoria, silica-beryllia, and silica-titania, as well as ternary combinations, such as silica-alumina-thoria, silica-alumina-zirconia, silica-alumina-magnesia and silica-magnesia-zirconia. The matrix may be in the form of a cogel. The relative proportions of finely divided zeolite and inorganic oxide gel matrix may vary widely, with the zeolite content ranging from between about 1 to about 99 percent by weight and more usually in the range of about 5 to about 80 percent by weight of the composite.

The process of this invention is conducted such that the organic reactants, i.e. the aromatic compound and the alkylating agent, are brought into contact with the zeolite in a suitable reaction zone, such as for example a fixed bed of the catalyst, under effective alkylation conditions. Such conditions include a temperature of between about 50° C. and about 500° C., a pressure of between about $2.5 \times 10^4$ N/m$^2$ and about $2.5 \times 10^7$ N/m$^2$ (0.25–250 atmospheres), and a feed weight hourly space velocity (WHSV) of between about 0.1 and about 500. The latter WHSV is based upon the weight of the catalyst compositions employed, i.e. the total weight of active catalyst and binder therefor. Preferred reaction conditions include a temperature within the approximate range of 100° C. to 350° C. with a feed WHSV of between 0.5 and 100. Although the reaction normally takes place at atmospheric pressure ($10^5$ N/m$^2$), the preferred pressure range extends from about $10^5$ N/m$^2$ to about $5 \times 10^6$ N/m$^2$. The reactants may be in either the vapor phase or the liquid phase and may be neat, i.e. free from intentional admixture or dilution with other material, or may be brought into contact with the zeolite with the aid of carrier gases or diluents such as, for example, hydrogen or nitrogen.

The alkylation process described herein may be carried out as a batch-type, semi-continuous or continuous operation utilizing a fixed or moving bed catalyst system. A preferred embodiment entails use of a catalyst zone wherein the hydrocarbon charge is passed concurrently or countercurrently through a moving bed of particle-form catalyst. The latter, after use, is conducted to a regeneration zone where coke is burned from the catalyst in an oxygen-containing atmosphere (such as air) at elevated temperature, after which the regenerated catalyst is recycled to the conversion zone for further contact with the organic reactants.

The following examples are provided to illustrate the process of this invention and to aid those in the art in the understanding thereof, but clearly should not be taken as presenting undue limitations thereon:

EXAMPLE 1

(ZSM-12)

Benzene was alkylated with octene-1 in the presence of zeolite HZSM-12 (silica/alumina ratio=90; 65 wt. % on alumina binder). The reaction was carried out in a flow reactor at 205° C. and 200 psig. The reactants, at a benzene/octene mole ratio of 4/1, were passed across the catalyst at a feed WHSV of 30 hr$^{-1}$. Analysis of the effluent indicated that, at 99% octene-1 conversion, selectivity to phenyloctane was 53%. Composition of the phenyloctanes was: 92% 2-phenyloctane, 7% 3-phenyloctane, and 1% 4-phenyloctane, with 69% being linear phenyloctanes.

EXAMPLE 2

(AlCl$_3$)

Using conventional Friedel-Crafts technology, benzene and octene-1 (mole ratio 8/1) were reacted with AlCl$_3$ catalyst at 30° C. and atmospheric pressure. Octene-1 conversion was 97% and selectivity to phenyloctane 73%. Isomeric composition of the phenyloctane was: 49% 2-phenyloctane, 28% 3-phenyloctane, and 23% 4-phenyloctane, and 100% thereof being linear phenyloctanes.

EXAMPLE 3

(Mordenite, dealuminized)

A sample of mordenite (Norton Zeolon Type 100 H, silica/alumina mole ratio=10) was air calcined for one hour at 400° C. followed by one hour at 600° C. The material was refluxed for 20 hours with 0.5 N HCl (50 ml of solution per gram of zeolite) and then refluxed for 20 hours with distilled water. The silica to alumina ratio of the resulting dealuminized mordenite was 93.

Benzene and octene-1 (mole ratio=4/1) were passed over a sample of the above material at a feed WHSV of 30 hr$^{-1}$, 198° C. and 200 psig. Conversion of the C$_8$= was 100% with 76% selectivity to phenyloctanes. Isomeric composition of the phenyloctanes was: 71.7% 2-phenyloctane, 28.3% 3-phenyloctane, and no detectable amount of 4-phenyloctane; 87% of the phenyloctane product was linear phenyloctanes.

EXAMPLE 4

(Mordenite, dealuminized)

Repeat of Example 3, except at a temperature of 155° C., pressure of 210 psig and WHSV=90 hr$^{-1}$. Octene conversion was 99.3% and selectivity to phenyloctane 77%. Isomeric phenyloctane composition was: 86.6% 2-phenyloctane, 13.4% 3-phenyloctane, and no detectable amount of 4-phenyloctane; 96% of the phenyloctanes were linear.

EXAMPLE 5

(ZSM-12, steamed)

A sample of the same HZSM-12 as was used in Example 1 was steamed prior to use by passing steam over the catalyst at a pressure of one atmosphere (absolute) at 538° C. for about seven hours. A benzene/octene-1 feed stream (mole ratio=8/1) was passed over the steamed catalyst at 194° C., 565 psig and WHSV of 30 hr$^{-1}$. Conversion of octene was 88% with 83% selectivity to phenyloctane. The phenyloctane composition was as follows: 93% 2-phenyloctane, 6% 3-phenyloctane, and 1% 4-phenyloctane; 81% linear phenyl-substituted octanes.

EXAMPLE 6

(ZSM-11)

A sample of synthetic zeolite HZSM-11 (U.S. Pat. No. 3,709,979), which has a major pore dimension of 5.5 A, was placed in a flow reactor at 256° C. A feed stream of benzene and octene-1 (mole ratio=4/1) was passed over the catalyst at 615 psig and a WHSV of 30 hr$^{-1}$. Conversion of octene-1 was 100%, but selectivity to phenyloctane was only 6%. Due to the low yield and the large number of products found, the isomeric phenyloctanes could not be positively identified.

As will be seen from the foregoing, zeolite catalysts within the scope of those utilizable in the present invention—i.e. ZSM-12 and mordenite—are shown to selectively produce 2-phenyloctane in preference to the 3- and 4-isomers, as compared to the conventional AlCl$_3$ catalyst. Conversion rates were high and the yield of the linear product excellent. Zeolite HZSM-11, which has a pore opening of less than the desired 6 to 7 angstroms, is shown to have poor selectivity to phenyloctanes in general.

EXAMPLES 7-14

In a series of runs utilizing various zeolite materials, benzene was alkylated with dodecene-1. The feed stream was a 4/1 mole ratio mixture of benzene and dodecene-1 which was passed across each of the catalysts at WHSV of 30 hr$^{-1}$. The reaction temperatures and pressures are shown in Table I below, as are the level of C$_{12}$= conversion and the selectivity to phenyldodecane. Table II summarizes the isomeric distribution of the phenyldodecane produced.

TABLE I

| | Catalyst comparison - Benzene + Dodecene-1 | | | | |
|---|---|---|---|---|---|
| Example | Zeolite | Major Pore Dimension | Temp. | Pressure | C$_{12}$= Conversion | Selectivity to $\phi$-C$_{12}$ |
| 7 | HZSM-12 | * | 200° C. | 190 psig | 54% | 63% |
| 8 | Mordenite** | 7.0A | 200° C. | 200 psig | 98% | 80% |
| 9 | Offretite | 6.4A | 250° C. | 620 psig | 97% | 73% |
| 10 | HZSM-4 | 7.4A | 205° C. | 210 psig | 92% | 73% |
| 11 | Beta | * | 250° C. | 600 psig | 38% | 47% |
| 12 | Linde L | 7.1A | 195° C. | 210 psig | 72% | 72% |
| 13 | HZSM-38 | * | 200° C. | 215 psig | 94% | 73% |
| 14 | REY | 7.4A | 200° C. | 220 psig | 89% | 85% |

NOTES:
*Pore size unknown.
**Dealuminized, see Example 3.

TABLE II

| Catalyst Comparison - Phenyldodecane Isomer Distribution | | | | | | | |
|---|---|---|---|---|---|---|---|
| Example | Catalyst | 2-$\phi$ | 3-$\phi$ | 4-$\phi$ | 5-$\phi$ | 6-$\phi$ | % Linear |
| 7 | HZSM-12 | 92% | 8% | 0 | 0 | 0 | 78% |
| 8 | Mordenite (-Al) | 85% | 15% | 0 | 0 | 0 | 95% |
| 9 | Offretite | 79% | 14% | 5% | 1% | 1% | 75% |
| 10 | HZSM-4 | 57% | 25% | 8% | 5% | 5% | 90% |
| 11 | Beta | 57% | 18% | 10% | 7% | 8% | 53% |
| 12 | Linde L | 40% | 18% | 16% | 15% | 11% | 88% |
| 13 | HZSM-38 | 37% | 19% | 13% | 14% | 16% | 78% |
| 14 | REY | 25% | 20% | 18% | 19% | 18% | 92% |

The zeolites of Examples 7–9, which come within the scope of those disclosed as being utilizable in the present invention, are seen to selectively produce the 2-phenyldodecane isomer in very high yields with little or none of the other isomers produced as side-products. In contrast, the larger pore size zeolites of Examples 10–14 are seen to produce a relatively broader spectrum of phenyldodecane isomers, making the 2-isomer difficult to isolate in significant amounts.

Having thus described the present invention with the aid of certain specific examples thereof, it is to be understood that such examples are intended to be merely illustrative of the disclosed process. Many variations thereon may be made without departing from the spirit of the disclosed invention, as will be evident to those skilled in the art, and such variations are intended to come within the scope of the following claims:

What is claimed is:

1. A process for the selective alkylation of an aromatic compound with a relatively long chain length alkylating agent to produce linear phenylalkanes enriched in the 2-phenylalkane isomer; said alkylating agent comprising an aliphatic or aromatic organic compound having one or more available reactive alkyl groups of at least five carbons in the linear hydrocarbon chain; said process comprising contacting said aromatic compound with said alkylating agent in the presence of a selective zeolite catalyst at a temperature of between about 50° C. and about 500° C. and a pressure within the approximate range of $2.5 \times 10^4$ N/m$^2$ to $2.5 \times 10^7$ N/m$^2$; said selective zeolite catalyst being characterized by a crystal structure having channels or network of pores therethru, the major dimension of the openings to said channels or networks of pores being between about 6 and about 7 angstroms.

2. A process as described in claim 1 wherein said alkyl groups have between about six and about twenty carbon atoms in the linear hydrocarbon chain.

3. A process as described in claim 1 wherein said aromatic compound is benzene.

4. A process as described in claim 1 wherein said aromatic compound comprises a benzene ring having from one to two substituents thereon.

5. A process as described in claim 1 wherein said temperature is within the approximate range of from 100° C. to 350° C. and said pressure is between about $10^5$ N/m$^2$ and about $5 \times 10^6$ N/m$^2$.

6. A process as described in claim 1 wherein said selective zeolite is chosen from the group consisting of: cancrinite, gmelinite, mordenite, offretite, ZSM-12 and synthetic and naturally occurring isotypes thereof.

7. A process as described in claim 1 wherein said selective zeolite has the crystal structure of mordenite.

8. A process as described in claim 1 wherein said selective zeolite has the crystal structure of offretite.

9. A process as described in claim 1 wherein said selective zeolite has the crystal structure of ZSM-12.

10. A process as described in claim 1 wherein said zeolite is steamed prior to use.

11. A process as described in claim 1, 6, 7, 8, 9 or 10 wherein said zeolite is combined with a binder therefor and wherein said alkylating agent comprises 1-olefin.

* * * * *